(12) United States Patent
Greep (10) Patent No.: US 6,685,704 B2
(45) Date of Patent: Feb. 3, 2004

(54) UTILIZATION OF AN ACTIVE CATALYST IN A SURFACE COATING OF AN ELECTROSURGICAL INSTRUMENT

(75) Inventor: Darcy W. Greep, South Jordan, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 0 days.

(21) Appl. No.: 10/083,431

(22) Filed: Feb. 26, 2002

(65) Prior Publication Data

US 2003/0163125 A1 Aug. 28, 2003

(51) Int. Cl.$^7$ ............................................. A61B 18/14
(52) U.S. Cl. ........................... 606/41; 606/45; 606/49
(58) Field of Search .............................. 606/41, 45, 49

(56) References Cited

U.S. PATENT DOCUMENTS

| 4,197,217 A | | 4/1980 | Gartshore et al. ............ 252/466 |
| 4,314,559 A | * | 2/1982 | Allen ........................... 606/45 |
| 4,509,327 A | | 4/1985 | Enga ............................ 60/274 |
| 4,754,754 A | | 7/1988 | Garito et al. ............. 128/303.14 |
| 4,785,807 A | | 11/1988 | Blanch .................... 128/303.14 |
| 5,030,218 A | * | 7/1991 | Alexander .................... 606/45 |
| 5,051,241 A | | 9/1991 | Pfefferle ....................... 422/180 |
| 5,197,962 A | * | 3/1993 | Sansom et al. ................ 606/45 |
| 5,295,978 A | | 3/1994 | Fan et al. ..................... 604/265 |
| 5,417,933 A | | 5/1995 | Pfefferle ....................... 422/171 |
| 5,509,899 A | | 4/1996 | Fan et al. ....................... 604/96 |
| 5,549,604 A | | 8/1996 | Sutcu et al. .................... 606/45 |
| 5,558,900 A | | 9/1996 | Fan et al. ..................... 427/2.28 |
| 5,589,545 A | | 12/1996 | Ramachandran et al. ... 525/184 |
| 5,702,387 A | * | 12/1997 | Arts et al. ..................... 606/45 |
| 5,713,895 A | | 2/1998 | Lontine et al. ................ 606/41 |
| 5,731,087 A | | 3/1998 | Fan et al. ..................... 428/412 |
| 5,800,427 A | * | 9/1998 | Zamba .......................... 606/39 |
| 5,885,281 A | * | 3/1999 | Urueta ......................... 606/45 |
| 5,925,039 A | * | 7/1999 | Landingham ................. 606/41 |
| 5,925,043 A | * | 7/1999 | Kumar et al. ................. 606/45 |
| 5,935,529 A | | 8/1999 | Saito et al. ................... 422/177 |
| 6,106,523 A | | 8/2000 | Morris .......................... 606/45 |
| 6,132,427 A | | 10/2000 | Jones et al. ................... 606/45 |
| 6,139,547 A | | 10/2000 | Lontine et al. ................ 606/41 |
| 6,270,831 B2 | | 8/2001 | Kumar et al. .............. 427/2.24 |
| 6,409,725 B1 | * | 6/2002 | Khandkar et al. ............. 606/45 |
| 6,544,596 B2 | | 4/2003 | Clemens et al. .......... 427/407.1 |
| 6,551,267 B1 | | 4/2003 | Cohen et al. ............... 604/6.15 |
| 6,558,686 B1 | | 5/2003 | Darouiche ................... 424/423 |
| 6,558,798 B2 | | 5/2003 | Zhong et al. ................ 428/420 |
| 6,559,132 B1 | | 5/2003 | Holmer ......................... 514/56 |
| 2001/0031964 A1 | * | 10/2001 | Gentelia et al. .............. 606/45 |
| 2003/0109864 A1 | * | 6/2003 | Greep et al. .................. 606/41 |
| 2003/0109865 A1 | * | 6/2003 | Greep et al. .................. 606/41 |

OTHER PUBLICATIONS

Mikos, A.G. et al., "Laminated Three–Dimensional Biodegradable Foams For Use In Tissue Engineering", 1993, Biomaterials, vol. 14, No. 5, pp 323–330.

Ikada, Ph.D., Y. et al. "Lubricious Polymer Surfaces", 1993, Lubricating Polymer Surfaces, pp 41–71.

* cited by examiner

Primary Examiner—Lee Cohen
(74) Attorney, Agent, or Firm—Workman Nydegger (57) ABSTRACT

Applying and utilizing a catalyst in a coating layer to enhance release of accumulated buildup on a surface. The catalyst is in the form of micro or nano-sized particles that are optionally mixed with a binder material and applied as a coating of at least a portion of a surface, such as an electrosurgical tip. The particles are located on the outer surface of the coating layer to be in direct contact with any buildup, such as eschar, that may have accumulated. An energy source, such as a heat source, a light source, a microwave source, or the like, is used to activate the catalyst in order to aid in the release of the accumulated eschar. The activated catalytic particles interact with the eschar constituents to break bonds that have occurred between the eschar and the surface of the electrode or tip, allowing the eschar to release from the tip.

34 Claims, 5 Drawing Sheets

UTILIZATION OF AN ACTIVE CATALYST IN A SURFACE COATING OF AN ELECTROSURGICAL INSTRUMENT

BACKGROUND OF THE INVENTION

1. The Field of the Invention

The present invention relates to coated electrosurgical instruments. More particular, the present invention relates to using catalytic particles in a coating layer of an electrosurgical instrument and activating the particles to release charred matter that may become accumulated on the instrument.

2. The Relevant Technology

In the area of electrosurgery, medical procedures of cutting tissue and/or cauterizing leaking blood vessels are performed by utilizing radio frequency (RF) electrical energy. The RF energy is produced by a signal generator and is transmitted to an electrode or tip coupled to a hand-piece, pencil, or electrode holder operated by a surgeon. The electrode or tip delivers an electrical discharge to cellular matter of the patient's body adjacent to the electrode or tip. The discharge causes the cellular matter to heat up in order to cut tissue and/or cauterize blood vessels.

The high temperature involved in electrosurgery can cause charred matter to form and become affixed to the electrode or tip. The buildup of charred matter can reduce the efficiency of the cutting and/or cauterizing processes by creating an insulating barrier that interferes with the transference of RF energy to the targeted area. By way of example, when cauterizing an are a to prevent bleeding, the charred matter can inhibit the cauterization, cause the destruction of additional tissue and increase thermal tissue damage. Thus, buildup of the charred matter can slow the surgical procedure, as the surgeon is required to remove the charred matter from the electrode or tip.

The application of a fluoropolymer as a coating layer on at least a portion of an electrosurgical electrode or tip has proven to be a valuable asset in providing additional properties to the electrode or tip, including providing a non-stick surface and a high temperature stability. However, while the anti-adhesion properties of fluoropolymers, such as polytetrafluoroethylene ("PTFE") or Teflon®, as a coating layer on an electrode or tip has facilitated electrosurgical cutting and/or cauterizing by reducing the buildup of debris on the electrode or tip, it has not completely eliminated such buildup. Accordingly, it would be an improvement in the art to augment or even replace the fluoropolymer coating with other anti-adhesion materials. Unfortunately, it has heretofore been difficult to adhere other materials to surfaces coated with a fluoropolymer having an anti-adhesion property.

BRIEF SUMMARY OF THE INVENTION

The present invention relates to the utilization of a catalyst in a surface coating. More specifically, the present invention relates to using catalytic particles in a coating layer of an electrosurgical instrument and activating the particles to release charred matter that has accumulated on the instrument.

Implementation of the present invention takes place in association with a surface, such as at least a portion of the surface of an electrosurgical electrode or tip that may be used to cut tissue and/or cauterize blood vessels of a patient during a surgical operation. At least a portion .of the electrode or tip is coated with an active catalyst, such as a noble metal, (e.g., platinum, palladium, titanium, etc.) and a binder material, such as a fluoropolymer, to provide a release of charred blood and/or tissue, known as eschar, which accumulates on the electrode or tip during an electrosurgical procedure.

The active catalyst is in the form of micro or nano-sized particles that are mixed with the binder material and the mixture is applied as a coating onto at least a portion of the electrode or tip In this manner, the catalytic particles are located on the outer surface of the coating layer to be in direct contact with any eschar that may have accumulated. An energy source, such as a heat source, a light source, microwave source, or other electromagnetic radiation or energy source cooperates with the electrosurgical instrument to activate the catalytic particles.

The active catalytic particle advance the release of accumulated eschar from the electrode or tip by interacting with the eschar constituents to reduce chemical absorption and/or bonding. The activated particles react with the carbon or nitrogen based materials in the accumulated eschar. As a result, bonds that have occurred between the eschar and the surface of the electrode or tip are broken, allowing the eschar to release from the electrode or tip.

While the methods and processes of the present invention have proven to be particularly useful in the area of electrosurgery, those skilled in the art can appreciate that the methods and processes of the present invention can be used on a variety of different kinds of surfaces and in a variety of different areas of manufacture to yield a coated surface that has desired properties for performing a particular task.

Additional features and advantages of the present invention will be set forth in the description which follows, and in part will be obvious from the description, or may be learned by the practice of the invention. Further, the features and advantages of the invention may be realized and obtained by means of the instruments and combinations particularly pointed out in the appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to the utilization of a catalyst in a surface coating. More specifically, the present invention relates to using catalytic particles in a coating layer of an electrosurgical electrode or tip that is used in conjunction with an electrosurgical pencil, holder, or handpiece. These particles are activated by an energy source to provide a release of charred matter that may become accumulated on the electrode or tip.

In the disclosure, reference is made to an electrosurgical electrode or tip. The use of these terms is interchangeable and refers to the portion of the electrosurgical instrument that contacts the tissue of a patient and through which the energy used to cut, coagulate and/or cauterize the tissue passes.

Further, in the disclosure reference is also made to the use of a fluoropolymer in a surface coating layer. In the disclosure and in the claims, the term "fluoropolymer" shall refer to a material that includes polymers that contain fluorocarbons or fluorinated hydrocarbons. By way of example, the term "Teflon®" represents a family of various fluoropolymers.

Additionally, in the disclosure and in the claims the term "binder" or "binder material" shall refer to a material that may be used with particles of an active catalyst to provide a surface coating on at least a portion of a surface. Examples of binder materials include a ceramic, a silicon, a metal, a polymer, such as a fluoropolymer, a sol gel deposition, and other such materials that are capable of withstanding high temperatures, such as the high temperatures required to perform electrosurgery, including a material that is a combination of an organic polymer or organic-polymer material and a ceramic or silicon.

The following disclosure of the present invention is grouped into three subheadings, namely "Exemplary Operating Environment," "Application of a Catalytic Coating Layer on a Surface" and "Activating the Catalytic Coating Layer." The utilization of the subheadings is for convenience of the reader only and is not to be construed as limiting in any sense.

Exemplary Operating Environment

Figure 1:
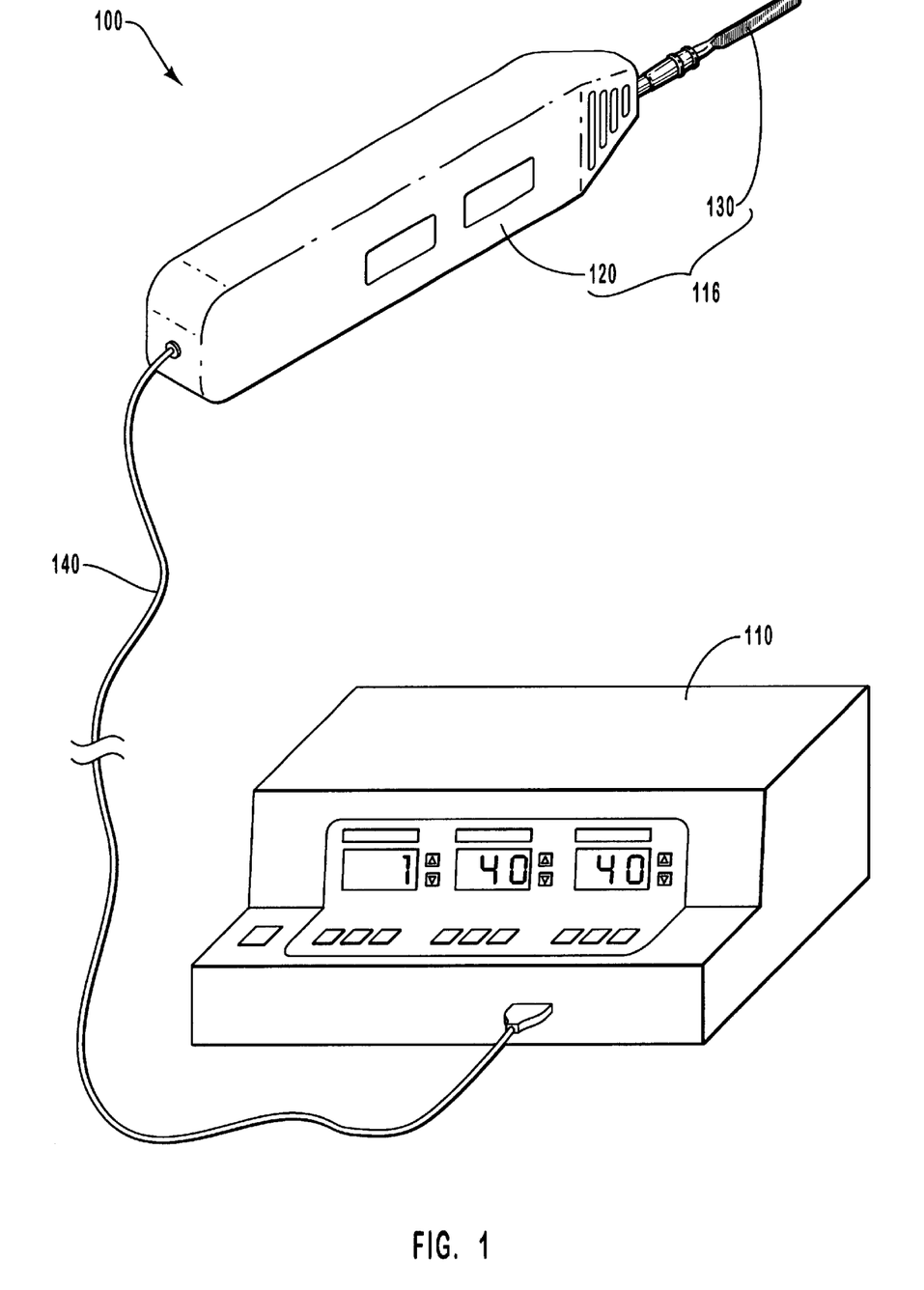
FIG. 1 illustrates an exemplary system that provides a suitable operating environment for use of the present invention.
Figure 2A:
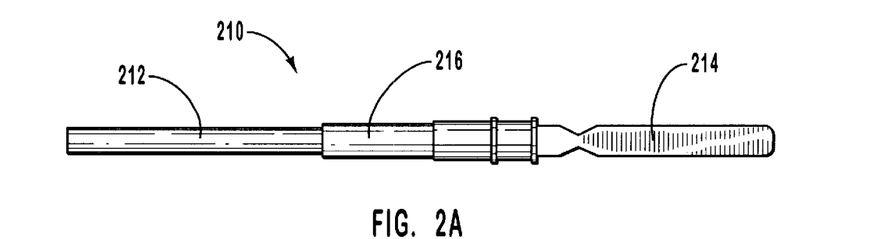
FIG. 2A illustrates an exemplary electrosurgical electrode or tip for use during electrosurgical procedures in the suitable operating environment of FIG. 1.
Figure 2B:
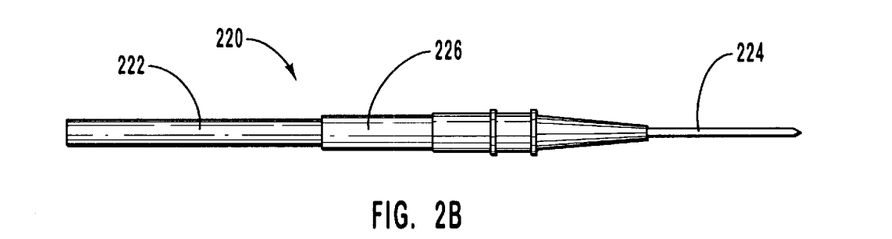
FIG. 2B illustrates another exemplary electrosurgical electrode or tip for use during electrosurgical procedures in the suitable operating environment of FIG. 1.
Figure 2C:
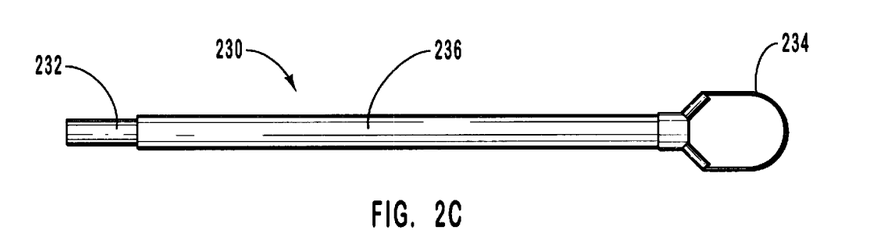
FIG. 2C illustrates still another exemplary electrosurgical electrode or tip for use during electrosurgical procedures in the suitable operating environment of FIG. 1.
Figure 2D:
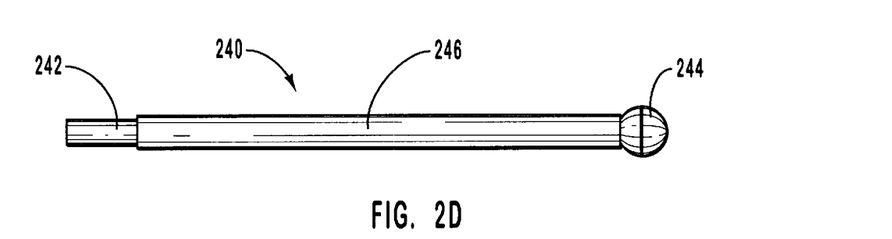
FIG. 2D illustrates yet another exemplary electrosurgical electrode or tip for use during electrosurgical procedures in the suitable operating environment of FIG. 1.
Figure 2E:
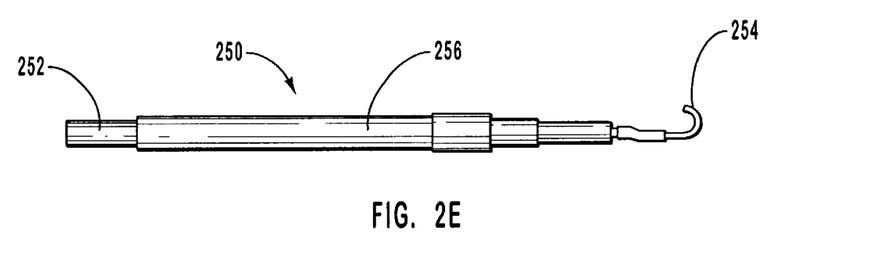
FIG. 2E illustrates another exemplary electrosurgical electrode or tip for use during electrosurgical procedures in the suitable operating environment of FIG. 1.

FIGS. 1–2E and the corresponding discussion are intended to provide a brief, general description, of a suitable operating environment in which the invention may be implemented. Although not required, the invention will be described in the general context of providing specific properties, attributes and/or characteristics at a surface area of an electrode or tip of an electrosurgical instrument. Those skilled in the art, however, will appreciate that embodiments of the present invention may be practiced in association with a variety of different surfaces in order to provide desirable properties, attributes and/or characteristics at the surfaces.

Referring to FIG. 1, an exemplary environment is illustrated that provides a suitable operating environment for use of the present invention. In FIG. 1, electrosurgical system 100 is illustrated, which includes a signal generator 110 and an electrosurgical instrument 116 electrically coupled to signal generator 110 though cord 140. A surgeon typically may use electrosurgical system 100 during surgical procedures to cut tissue, coagulate blood, and/or cauterize blood vessels of a patient's body. Although reference is made to embodiments of the present invention cutting tissue and/or cauterizing blood vessels, it can be understood that the same electrosurgical instruments are capable of coagulating tissue, blood vessels, and the blood or other fluids flowing through the tissue and/or blood vessel. Therefore, reference to cutting tissues and/or cauterizing blood vessels includes coagulating portions of the patient's body.

In electrosurgery, radio frequency (RF) electrical energy is produced by a signal generator, such as signal generator 110, and is introduced to a patient's body by electrosurgical instrument 116. More specifically, the radio frequency energy is introduced to the patient's body through an electrode or tip 130 electrically coupled to a hand piece 120; the combination of tip 130 and hand piece 120 forms an exemplary electrosurgical instrument 116. The RF electrical energy generated by signal generator 110 is transmitted from signal generator 110 to tip 130 though hand piece 120 and cord 140. An electrical discharge is delivered from tip 130 to the patient to cause the heating of cellular matter of the patient that is in extremely close contact to tip 130. The heating takes place at an appropriately high temperature to allow performance of electrosurgery using hand piece 120 and tip 130. A grounding electrode may be employed to carry excess charge that is dissipated into surrounding tissue of the patient's body away from the patient.

During electrosurgery, tip 130 may be used to independently or concurrently cut and cauterize. A constant sinusoidal signal supplied by signal generator 110 and transmitted to tip 130 through hand piece 120 allows tip 130 to cut through tissue of the and transmitted to tip 130 through hand piece 120 allows tip 130 to cauterize leaking blood vessels. A combination of the constant sinusoidal signal and the damped wave signal can be supplied by signal generator 110 to tip 130 through hand piece 120 for allowing tip 130 to concurrently cut and cauterize, thereby minimizing tissue trauma and blood loss during the surgical procedure.

FIGS. 2A–2E illustrate an exemplary assortment of interchangeable tips for use with hand piece 120 to facilitate the acts of cutting tissue and/or cauterizing blood vessels. Each of the interchangeable tips has a first end that can be coupled to hand piece 120, an insulator, and a second end that applies the discharge to the patient's body. The configuration of the second end allows for a great versatility of the acts of cutting and/or cauterizing in a variety of different surgical procedures. Although reference is made to interchangeable tips, one skilled in the art can appreciate that alternate embodiments of the present invention can utilize tips that are attached to the hand piece and are non-removable therefrom.

By way of example, FIG. 2A illustrates tip 210, which is a tip that may be used in general surgery for cutting tissue and/or for cauterizing blood vessels. End 212 is coupled to the hand piece 120 to allow the RF electrical energy, generated from the signal generator and transmitted to the hand piece 120, to be transmitted through tip 210. A discharge is delivered to the patient's body from end 214, which is in a blade-like configuration. End 214 has two parallel sides that are flat to allow end 214 to function in a similar manner as traditional scalpel. However, rather than employing a mechanical action for cutting through tissue, the electrical discharge allows end 214 to slide through the tissue as the tissue is being superheated to an appropriate temperature to perform the electrosurgical procedure. A coating 216 surrounds at least a portion of tip 210 and acts as an insulator.

Similarly, FIG. 2B illustrates tip 220, which may be used for cutting tissue and cauterizing leaking blood vessels in particularly dense areas of a patient's body, such as those experienced in cerebral operations. End 222 is coupled to the hand piece 120 to allow the RF electrical energy, generated from the signal generator and transmitted to the hand piece 120, to be transmitted through tip 220. A discharge is delivered to the patient's body from end 224, which is in a needle-like configuration that comes to a point to allow for very accurate surgical procedures in dense areas of the patient's body. A coating 226 surrounds at least a portion of tip 220 and acts as an insulator. Through the use of tip 220, delicate cerebral tissues can be accurately removed with virtually no damage to any surrounding membranes and with minimal bleeding and/or swelling resulting from the procedure.

FIG. 2C illustrates tip 230, which may be used for the removal of large sections of tissue, as in, for example, prostate and tumor excision. End 232 is coupled to the hand piece 120 to allow the RF electrical energy to be transmitted through tip 230. A discharge is delivered to the patient's body from end 234, which is in a loop-like configuration. A coating 236 surrounds at least a portion of tip 230 and acts as an insulator.

FIG. 2D illustrates tip 240, which may be used to specifically cauterize leaking blood vessels and to seal open structures. End 242 is coupled to the hand piece 120 to allow the RF electrical energy to be transmitted through tip 240. A discharge is delivered to the patient's body from end 244, which is in a spherical configuration. A coating 246 surrounds at least a portion of tip 240 and acts as an insulator.

FIG. 2E illustrates tip 250, which may facilitate a surgeon in reducing extraneous tissue damage by allowing individual tissues or blood vessels to be isolated and independently cut and/or cauterized. End 252 is coupled to the hand piece 120 to allow the RF electrical energy from the signal generator to be transmitted through tip 250. A discharge is delivered to the patient's body from end 254, which is in a hook-like configuration. A coating 256 surrounds at least a portion of tip 250 and acts as an insulator.

Ends 214, 224, 234, 244 and 254 are examples of surfaces upon which a coating may be applied to provide desirable properties at the surface. For example, when the surface is at least a portion of an electrosurgical electrode or tip, an example of a desired property may include enabling a release of eschar that may otherwise have accumulated on the electrosurgical electrode or tip. The release of accumulated eschar allows for a more efficient use of the electrode or tip by reducing damage to surrounding tissues that may have been otherwise caused by eschar accumulation on the electrode or tip during an electrosurgical procedure.

Application of a Catalytic Coating Layer on a Surface

A surface coating that includes a catalyst, such as a noble metal (e.g., platinum, palladium, titanium, etc.), may be applied to a surface and activated to enable a release of charred matter that has accumulated on the surface. The catalyst may be in the form of micro-sized or nano-sized particles, such that the diameter of the particles is of the approximate order of about $10^{-9}$ to about $10^{-6}$ meter (i.e., about 1 nanometer to about 1 micron). The particles may be mixed with a binder material, such as a ceramic, a silicon, a metal, a polymer, such as a fluoropolymer, a sol gel deposition, and/or another material that is capable of withstanding high temperatures, such as the high temperatures required to perform electrosurgery, prior to being applied to the surface as a coating layer. Alternatively, the catalytic particles may be layered directly onto the surface.

As provided above, one embodiment includes the use of a noble metal as a catalytic particle. A noble or precious metal is one of a group of eight elements that have some physical characteristics in common. The elements are highly resistant to oxidation and corrosion and hence are referred to as being "noble." The elements are characteristically soft, ductile and heat resistant. The noble metals include silver, gold, platinum, palladium, rhodium, ruthenium, iridium and osmium.

Figure 3A:
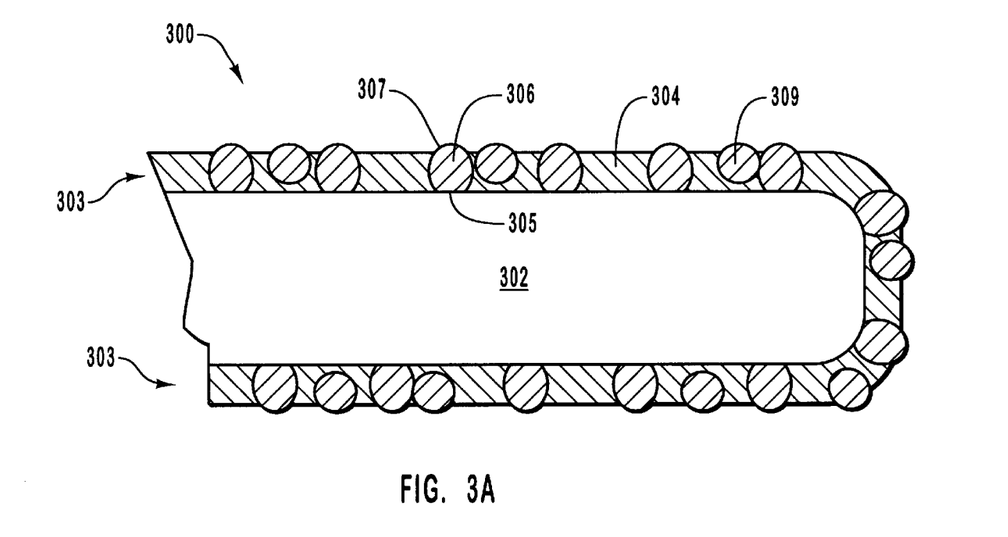
FIG. 3A illustrates an exemplary cross-sectional view of an electrosurgical electrode or tip that has a coating layer applied thereon that includes active catalyst particles and a binder material.

With reference to FIG. 3A, an exemplary cross-sectional view of an electrosurgical electrode or tip is illustrated as tip 300, which includes a substrate 302 that may receive a catalytic coating layer on at least a portion thereof. Substrate 302 is capable of conducting the RF energy during an electrosurgical procedure. The substrate 302 can be metallic, such as but not limited to surgical stainless steel, some other composition of conductive and non-conductive materials, or the like, so long as substrate 302 allows RF energy to be transferred from hand piece 120 to tip 300 and from tip 300 to the patient.

The surface of substrate 302 may be prepared for receiving a catalytic coating layer thereon, such as by being heat cleaned in order to remove any oils or contaminants and may be roughened to provide a footing for particles of the coating layer. Once the surface of the substrate is prepared, in one embodiment, a catalytic coating layer is layered directly thereon. By way of example, catalytic particles may be layered onto the substrate through the use of a sputter technique. The catalytic particles bond to the substrate and at least a portion of the catalytic particles are exposed in order to react with accumulated eschar when activated, as will be further explained below.

In another embodiment, and as illustrated in FIG. 3A, catalytic particles are mixed with a binder material, such as particles of a fluoropolymer, prior to being applied to substrate 302. Once the catalytic particles are mixed with the fluoropolymer particles, a suspension of the mixed particles and an etching agent may be spray-coated onto the substrate 302 so as to uniformly apply a catalytic coating layer, illustrated in FIG. 3A as coating layer 303, to at least a portion of substrate 302. The etching agent improves the bond between the mixed particles and the substrate 302.

Coating layer 303 includes catalytic particles, such as particle 306, and a binder material 304, which in one embodiment is less than or equal to the diameter of the catalytic particles to allow at least a portion of the catalytic particles to be exposed or located on the outer surface of the coating layer 303, as illustrated in FIG. 3A. As such, the catalytic particles are able to be in direct contact with eschar that may have accumulated on the tip 300. Therefore, with reference to active catalytic particle 306, a first end 305 of particle 306 may be in contact with the substrate 302 and since the binder material 304 is less than or equal to the diameter of the particle 306, a second end 307 is exposed in order to allow the particle 306 to interact with and cause a release of accumulated eschar on tip 300. While particle 306 is in contact with substrate 302, other catalytic particles may not be in contact with the substrate 302, such as particle 309.

A catalytic particle may be able at a certain point, such as at an edge of a crystal or at a single atom, supply a charge (e.g., an electron) to the material (e.g., the eschar) that is being catalyzed. The catalytic particles bond to the eschar and are activated by an energy source to cause a catalysis to occur, which breaks down the large hydrocarbon molecules into shorter units, specifically where the eschar attaches to the material of the electrode or tip. As such, the catalytic particles break the bonds between the eschar and the electrosurgical electrode or tip and allows the eschar to release from the surface of the electrode or tip, as will be further explained below.

Figure 3B:
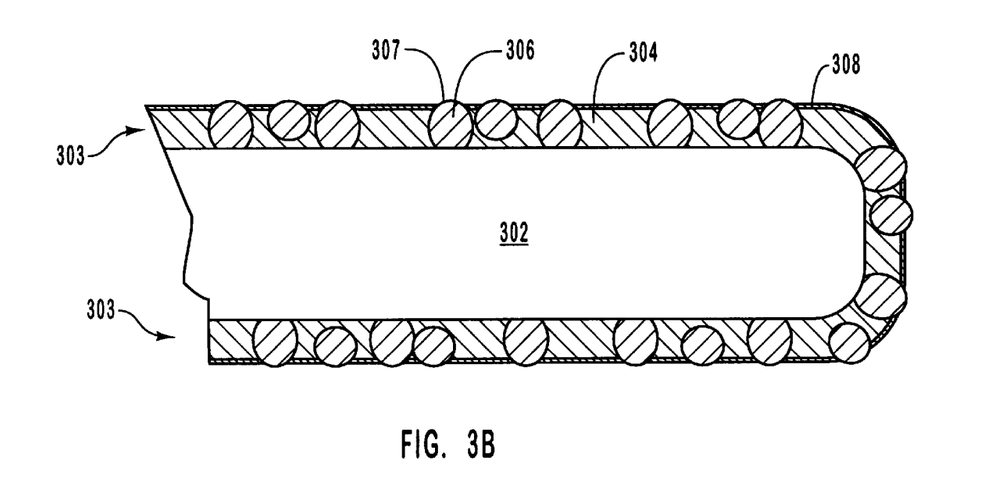
FIG. 3B illustrates an exemplary cross-sectional view of the electrosurgical electrode or tip of FIG. 3A that further includes a covering layer applied thereon.

When the binder material 304 that is used to create coating layer 303 is an anti-adhesion material, such as an anti-adhesion fluoropolymer, the binder material 304 provides a non-stick portion of coating layer 303 that reduces the amount of eschar accumulation on tip 300 during an electrosurgical procedure. While the present example includes a binder material that includes a fluoropolymer, other binder materials may be used together with catalytic particles to create a coating layer, such as a ceramic, a silicon, a metal, a sol gel deposition, and/or other materials that are capable of withstanding the high temperatures of electrosurgery, including a hybrid-material that is a combination of an organic polymer, or organic-polymer material and a ceramic or silicon, as provided above. With reference to FIG. 3B, an additional coating layer 308 may optionally be applied onto the binder material 304 that allows at least a portion of the catalytic particles to remain exposed, such as end 307 of particle 306, and that provides additional properties, attributes and/or characteristics to the surface of the electrode or tip. For example, the coating layer 308 may include a water-soluble polymer, such as polyethylene oxide ("PEO"), polyethylene glycol ("PEG"), or the like, which typically causes an attraction of Water to the surface.

The attraction of water at an electrosurgical electrode or tip may provide various useful purposes in the area of electrosurgery. For example, the attraction of water may assist in cooling the tip by evaporation during use of the tip, thereby protecting and prolonging the service life of the binder material 304 on the tip. The attraction of water may also act as a lubricant for an enhanced release character of the binder material 304. The presence of the water-soluble polymer may also provide a low shear, sacrificial layer during tip cleaning that can serve to protect and enhance the activity of the binder material 304. The water-soluble polymer may also act to supply a radical scavenger or inhibitor to reduce damage done to the binder material 304 during a process of gamma sterilization, thereby improving the properties and service life of the binder material 304. Furthermore, the water-soluble polymer may act as a carrier of antibiotic factors, healing factors, anti-adhesion factors, anti-tumor factors, tumor necrosis factors, and the like, which are specifically included in the coating of the tip as desired, and by design, for deposition in and on tissues of a patient's body where electrosurgical procedures are performed.

Activating the Catalytic Coating Layer

Catalytic particles of a coating layer may be activated to advance a release of accumulated eschar from the surface of an electrosurgical electrode or tip. An energy source, such as a heat source, a light source, a microwave source, or other electromagnetic radiation or energy source, may be coupled to or communicate with the electrosurgical instrument to activate the catalytic particles. The active catalytic particles break bonds between the eschar and the surface of the tip, allowing the eschar to release from the tip.

In one embodiment, and with reference to FIG. 1, the energy source that activates the catalytic particles of a surface coating layer on the tip is signal generator 110. The signal generator 110 provides RF electrical energy to hand piece 120 and the corresponding tip 130. The RF electrical energy powers hand piece 120 so that an electrical discharge is delivered from tip 130 to heat cellular matter of the patient in extremely close contact to the tip 130, while activating the catalytic particles of surface coating layer of the tip 130. The heating takes place at an appropriately high temperature to allow tip 130 to be used to perform electrosurgery and to activate the catalytic particles. By way of example, the process of activating catalytic particles may take place at temperatures greater than 300° C. and the electrosurgical system 100 may generate temperatures over 800° C. To improve the capabilities of tip 130 to activate the catalytic particles, an electrically resistive coating that heats up in response to the buildup of eschar may be applied on the tip. This electrically resistive coating acts as an energy source, whether alone or in combination with signal generator 110. For instance, the electrically resistive coating can be a metallic coating, such as but not limited to tungsten, which acts as a resistive heater upon the coating receiving a portion of the RF signal received by tip 110. Alternatively, the electrically resistive coating can be connected to a separate power source that causes heating of the electrically resistive coating, thereby activating the catalytic particles.

In another configuration, the electrically resistive coating can be a ceramic coating that generates heat in response to receiving a portion of the RF energy from generator 110 and/or from receiving energy from a separate power source. Illustrative ceramic coatings are provided by ThermoCeramiX, LLC. In still another configuration, a thin film heater coating is used as the electrically resistive coating, such as those thin film heater coatings provided by Thermo Stone USA, LLC.

Figure 4A:
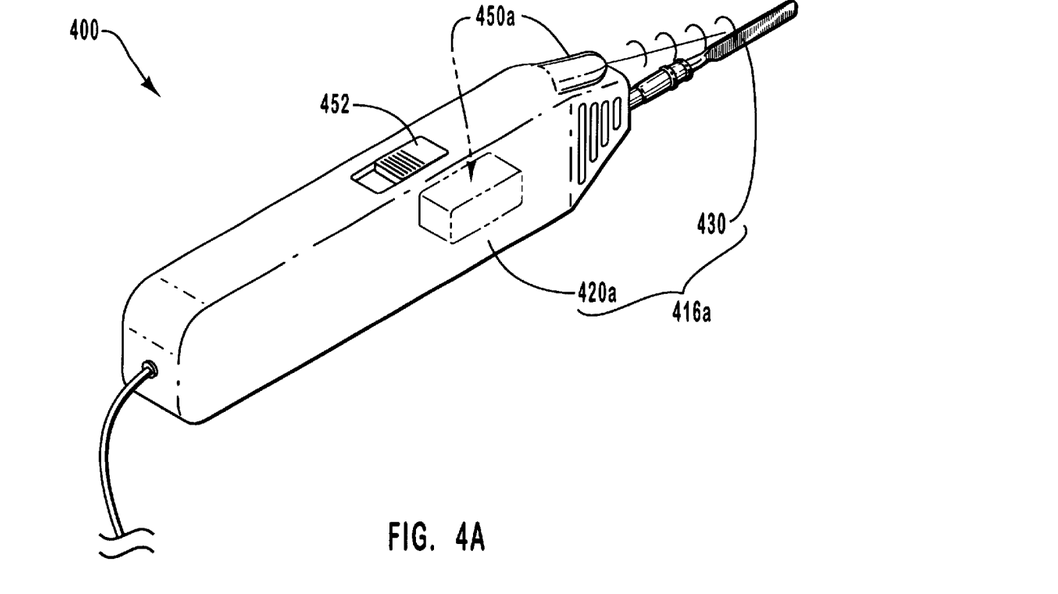
FIG. 4A illustrates an exemplary electromagnetic radiation or energy source in accordance with another aspect of the present invention.

Alternative embodiments embrace a variety of other types of energy sources that are capable of generating the energy to activate the catalytic particles. For example, as illustrated in FIG. 4A, a heat source, a light source, microwave source, or other applicable electromagnetic radiation or energy source may be coupled to an electrosurgical instrument 416a to provide the activation energy. The energy source, referenced by numeral 450a, directs electromagnetic radiation towards a tip 430 to activate the catalytic particles. A button 452 included in hand-piece 420 can activate the energy source to present the electromagnetic radiation to electrode 430. Alternatively, hand piece 420 and/or signal generator 410 can automatically activate energy source 450a immediately following generator de-activation or at some other predetermined time to activate the catalytic particles. For instance, in another configuration, a sensor (not shown) at generator 110 (FIG. 1) identifies when the energy transfer to the tissue of a patient is reduced, such as when there is a build-up of eschar on tip 430. When this occurs, the sensor activates energy source 450a to present electromagnetic radiation or energy to tip 430 to initiate catalytic activation and eschar removal.

In another configuration, a sensor notifies the physician of limited energy transfer to the patient's tissue, thereby suggesting eschar build-up on tip 430. Upon receiving the notification, such as an audible signal, a tactile signal, and/or a visual signal, the physician activates energy source 450*a* to direct electromagnetic radiation towards tip 430 to activate the catalytic particles.

Although FIG. 4A depicts electrosurgical instrument 416*a* as having energy source 450*a* protruding from hand-piece 420, one skilled in the art can identify other appropriate configurations. For instance, hand-piece 420 can be fabricated from a transparent material that allows electromagnetic radiation from an internal energy source, illustrated in dotted lines in FIG. 4A, to present such radiation to electrode 430 to activate the catalytic particles. As mentioned the electromagnetic radiation or energy can be heat energy, light energy, microwave energy, infrared energy, or other electromagnetic radiation or energy known to one skilled in the art in light of the teaching contained herein. Similarly, an internal electromagnetic radiation or energy source can be in contact with the electrode or tip.

Figure 4B:
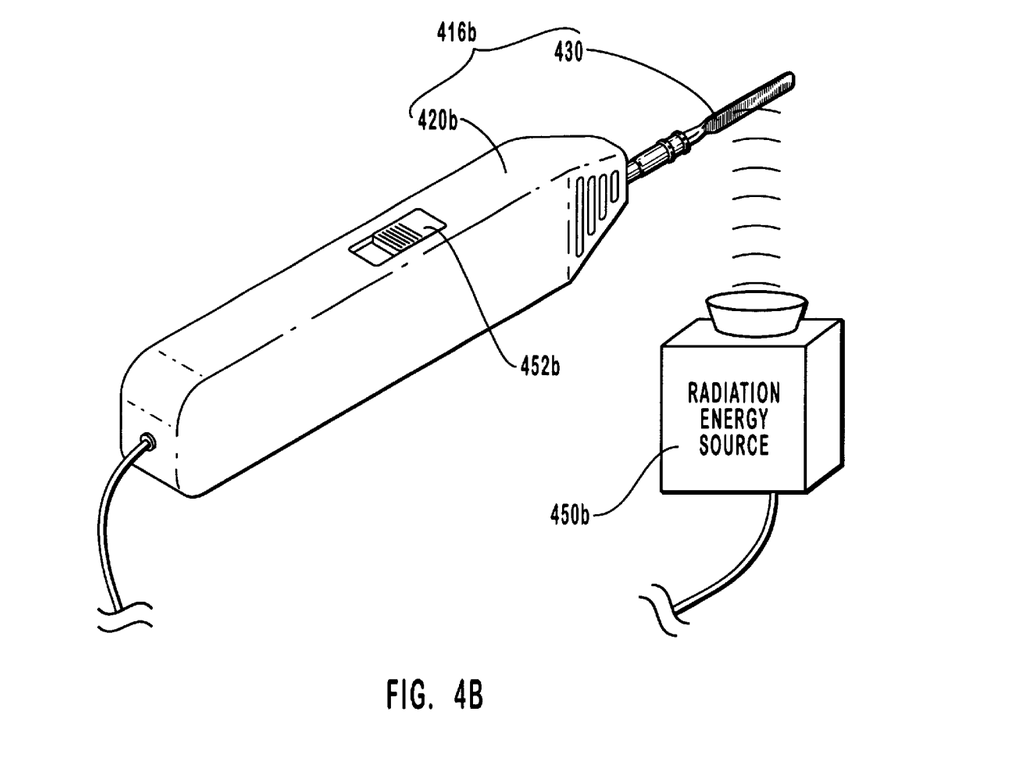
FIG. 4B illustrates another exemplary electromagnetic radiation or energy source in accordance with another aspect of the present invention.

In another configuration, as illustrated in FIG. 4B, a heat, a light, a microwave, or other electromagnetic radiation or energy source, referenced by numeral 450*b*, is separated from electrosurgical instrument 416*b*, while presenting heat energy, light energy, microwave energy, infrared energy, or other electromagnetic radiation or energy to electrosurgical instrument 416*b*. The source 450*b* presents electromagnetic radiation or energy to electrode 430 automatically and/or upon manipulation of button 452*b*.

Figure 4C:
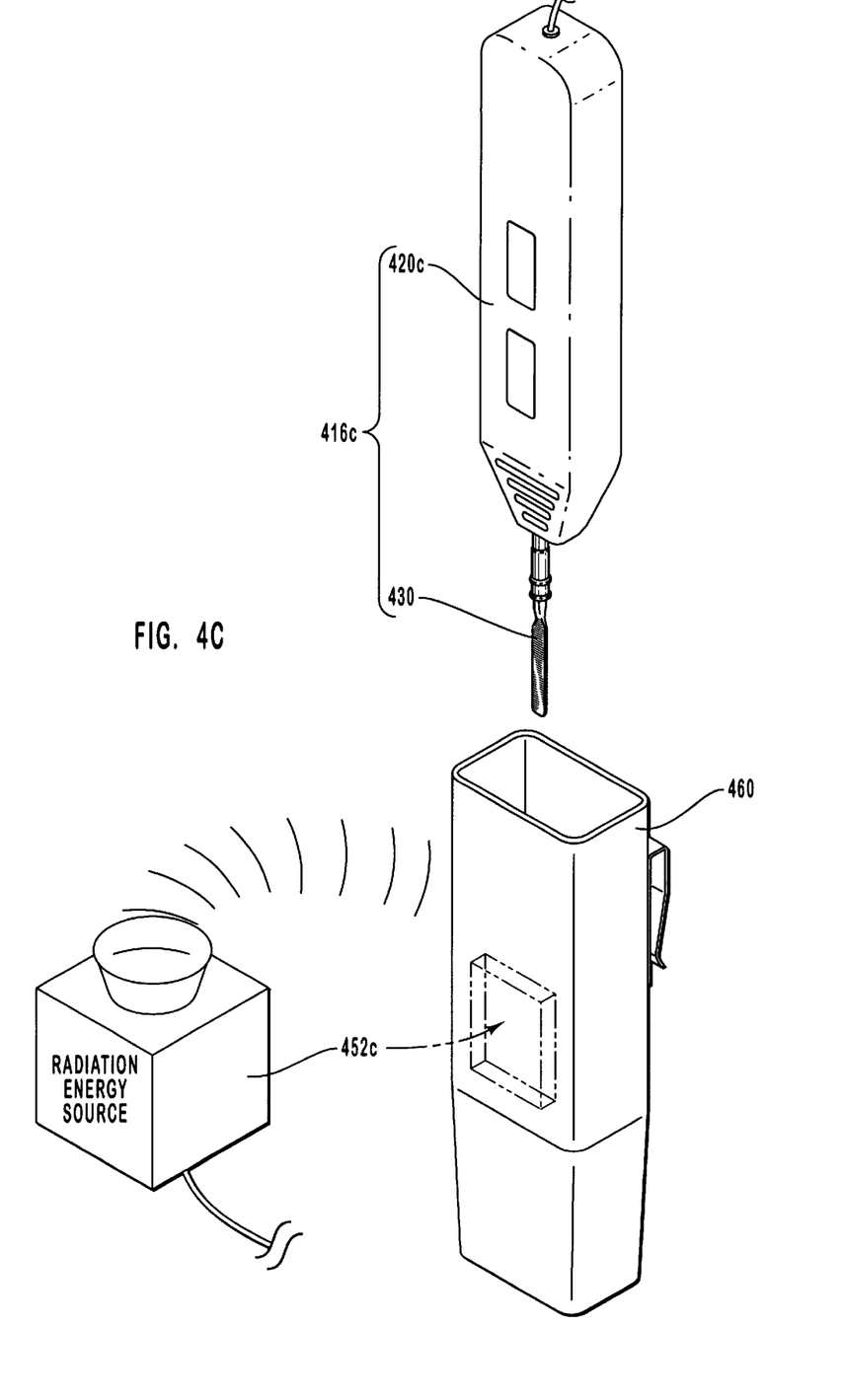
FIG. 4C illustrates another exemplary electromagnetic radiation or energy source in accordance with another aspect of the present invention.

In another configuration, as illustrated in FIG. 4C, the catalytic particles of an electrode 430 of an electrosurgical instrument 416*c* are activated upon placing electrosurgical instrument 416*c* into a holster 460. Although reference is made to holster 460, it can be appreciated by one skilled in the art in light of the teaching contained herein that a similar discussion can be made for any carrier or holder within which an electrosurgical instrument may be placed.

As depicted, holster 460 is transparent to the electromagnetic radiation generated by an electromagnetic radiation source 452*c*. This electromagnetic radiation can include, but not limited to, heat, light, microwave radiation, infrared radiation, or other electromagnetic radiation. Alternatively, as illustrated schematically by dotted lines in FIG. 4C, holster 460 can incorporate an electromagnetic radiation or energy source that delivers electromagnetic radiation or energy to electrode 430 when electrode 430 is disposed within holster 460.

No matter the particular manner by which the catalytic particles are activated, when the catalytic particles are activated, the active particles interact with the accumulated eschar constituents. The active catalytic particles react with the carbon or nitrogen based materials in the eschar that may have accumulated on the electrode or tip during an electrosurgical procedure. This reaction reduces the chemical absorption and/or bonding between the accumulated eschar and the electrode or tip, thereby enhancing a release of the eschar from the electrode or tip.

Thus, as discussed herein, the embodiments of the present invention embrace the application and utilization of a catalytic material on a surface. At least a portion of the surface, such as an electrosurgical electrode or tip, is coated with catalytic particles and optionally a binder material. The catalytic particles may be activated by a radiation or energy source to provide a release of charred blood and/or tissue, known as eschar, which accumulates at the electrode or tip during an electrosurgical procedure. The release of the eschar from the electrode or tip surface occurs as the active catalytic particles break bonds that have formed between the charred matter and the surface.

While the methods and processes of the present invention are particularly useful in the area of electrosurgery, those skilled in the art can appreciate that the methods and processes of the present invention can be used on a variety of different kinds of surfaces and in a variety of different areas of manufacture to yield a coated surface that has desired properties for performing a particular task.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. An electrosurgical instrument for use with an electrosurgical generator, the electrosurgical instrument comprising:
   a hand piece configured to receive energy from the electrosurgical generator; and
   a conductive tip adapted to receive the energy from the hand piece, the conductive tip comprising a coating, on at least a portion of the tip, which includes one or more catalytic particles, the catalytic particles having a diameter of about 1 nanometer to about 1 micron.

2. An electrosurgical instrument as defined in claim 1, wherein the one or more catalytic particles comprise at least one noble metal.

3. An electrosurgical instrument as defined in claim 2, where the noble metal includes at least one of silver, gold, platinum, palladium, rhodium, ruthenium, iridium, or osmium.

4. An electrosurgical instrument as recited in claim 1, further comprising an energy source communicating with at least one of the hand piece and the tip, the energy source being adapted to activate the catalytic particles to cause the activated catalytic particles to interact with eschar accumulated on the tip during an electrosurgical procedure and break one or more bonds between the eschar to release the eschar from the tip.

5. An electrosurgical instrument as recited in claim 4, wherein the energy source comprises at least one of a heat source, an electrically resistive coating applied to the tip, a light source, a microwave source, or an electromagnetic radiation source.

6. An electrosurgical instrument as recited in claim 1, wherein the coating further comprises a binder material.

7. An electrosurgical instrument as recited in claim 6, wherein the binder material includes at least one of:
   a fluoropolymer;
   a ceramic;
   silicon;
   a metal;
   a sol gel deposition; or
   a material that includes at least one of an organic polymer, a ceramic, or silicon.

8. An electrosurgical instrument as recited in claim 6, wherein the coating further comprises a water-soluble polymer.

9. An electrosurgical instrument as recited in claim 8, wherein the water-soluble polymer supplies a radical scavenger that reduces damage to the binder material during a process of gamma sterilization.

10. An electrosurgical instrument as recited in claim 8, wherein the water-soluble polymer is a carrier that deposits a factor on a contact area of a patient's body during an electrosurgical procedure.

11. An electrosurgical instrument as recited in claim 10, wherein the factor includes at least one of an antibiotic factor, a healing factor, an anti-adhesion factor, an anti-tumor factor, or a tumor necrosis factor.

12. An electrosurgical instrument as recited in claim 8, wherein the water-soluble polymer provides a low shear, sacrificial layer to the tip.

13. An electrosurgical instrument as recited in claim 1, wherein the coating further includes an etching agent.

14. A tip for use in performing an electrosurgical procedure, the tip comprising:
   a substrate; and
   a coating applied to at least a portion of the substrate, wherein the coating includes one or more catalytic particles, the catalytic particles having a diameter of about 1 nanometer to about 1 micron.

15. A tip as recited in claim 14, wherein the substrate includes a metal.

16. A tip as recited in claim 15, wherein the metal comprises surgical stainless steel.

17. A tip as recited in claim 15, wherein the metal comprises a roughened metal.

18. A tip as recited in claim 14, wherein the coating further includes a binder material and wherein one or more catalytic particles comprise at least one noble metal selected form the group consisting of silver, gold, platinum, palladium, rhodium, ruthenium, iridium, and osmium.

19. A tip as recited in claim 18, wherein the binder material includes at least one of:
   a fluoropolymer;
   a ceramic;
   silicon;
   a metal;
   a sol gel deposition; or
   a material that includes at least one of an organic polymer, a ceramic, or silicon.

20. A tip as recited in claim 18, wherein the coating further includes a water-soluble polymer that comprises at least one of polyethylene oxide, or polyethylene glycol, said water-soluble polymer acting as:
   a radical scavenger supplier that reduces damage to the binder material during a process of gamma sterilization;
   a carrier that deposits a factor during an electrosurgical procedure; and
   a low shear, sacrificial layer.

21. A method for coating an electrosurgical tip, the method comprising:
   providing an electrosurgical tip; and
   applying one or more catalytic particles to the tip, the catalytic particles having a diameter of about 1 nanometer to about 1 micron.

22. A method as recited in claim 21, wherein the tip is metallic, and the catalytic particles are applied using a sputter technique to embed the catalytic particles on at least a portion of the metallic tip.

23. A method as recited in claim 21, further comprising mixing the catalytic particles with a binder material prior to application of the catalytic particles and binder material to the tip in a first coating.

24. A method as recited in claim 23, further comprising mixing the mixture of catalytic particles and binder material with an etching agent prior to application to the tip.

25. A method as recited in claim 24, wherein the mixture is applied by at least one of a spray process or a dip process.

26. A method as recited in claim 23, further comprising applying a second coating over the first coating, wherein the second coating includes a water-soluble polymer.

27. A method as recited in claim 23, wherein the binder material includes at least one of:
   a fluoropolymer;
   a ceramic;
   silicon;
   a metal;
   a sol gel deposition; or
   a material that includes at least one of an organic polymer, a ceramic, or silicon.

28. An electrosurgical instrument for use with an electrosurgical generator, the electrosurgical instrument comprising:
   a hand piece configured to receive energy from the electrosurgical generator; and
   a conductive tip adapted to receive the energy from the hand piece, the conductive tip comprising a coating, on at least a portion of the tip, which includes one or more catalytic particles and a water-soluble polymer.

29. An electrosurgical instrument as recited in claim 28, wherein the water-soluble polymer provides a low shear, sacrificial layer to the tip.

30. An electrosurgical instrument as recited in claim 28, wherein the water-soluble polymer is a carrier that deposits a factor on a contact area of a patient's body during an electrosurgical procedure.

31. An electrosurgical instrument as recited in claim 30, wherein the factor includes at least one of an antibiotic factor, a healing factor, an anti-adhesion factor, an anti-tumor factor, or a tumor necrosis factor.

32. A tip for use in performing an electrosurgical procedure, the tip comprising:
   a substrate; and
   a coating applied to at least a portion of the substrate, wherein the coating includes one or more catalytic particles and a water-soluble polymer.

33. A tip for use in performing an electrosurgical procedure, the tip comprising: a substrate;
   a first coating over at least a portion of the substrate, the first coating comprising a plurality of catalytic particles and a binder material; and
   a second coating over the first coating, the second coating comprising a water-soluble polymer.

34. A tip as recited in claim 33, wherein the water-soluble polymer supplies a radical scavenger that reduces damage to the binder material during a process of gamma sterilization.

* * * * *